United States Patent [19]

Paul

[11] Patent Number: 4,748,110

[45] Date of Patent: May 31, 1988

[54] IMMUNOASSAY FOR HTLV-III ANTIGENS

[75] Inventor: Deborah A. Paul, Gurnee, Ill.

[73] Assignee: Abbott Laboratories, North Chicago, Ill.

[21] Appl. No.: 779,892

[22] Filed: Sep. 25, 1985

[51] Int. Cl.[4] .................. C12Q 1/70; G01N 33/53
[52] U.S. Cl. ............................ 435/5; 435/7; 435/28; 436/513; 436/531
[58] Field of Search ............... 435/28, 7, 5; 436/513, 436/531

[56] References Cited

U.S. PATENT DOCUMENTS 4,002,532  1/1977  Weltman et al. .................. 436/513

Primary Examiner—Sam Rosen
Attorney, Agent, or Firm—Martin L. Katz

[57] ABSTRACT

The invention is a diagnostic immunoassay which detects human T-cell lymphotropic virus-III (HTLV-III) antigen. The immunoassay utilizes a sandwich assay technique and the addition of a labeled second antibody to increase sensitivity. The second antibody is from an animal species different from the first.

6 Claims, No Drawings

IMMUNOASSAY FOR HTLV-III ANTIGENS

BACKGROUND OF INVENTION

The identification of human T-cell lymphotropic virus-III (HTLV-III) as the probable etiologic agent of acquired immune deficiency syndrome (AIDS) has led to development of diagnostic assays for detection of antibody to HTLV-III (anti-HTLV-III) in serum or plasma. In U.S. Pat. No. 4,520,113 such an immunoassay for HTLV-III antibody is described. Subsequently, Gallo et al., *Science,* 224: 500–503 (1984), have reported isolation of HTLV-III virus from a majority of anti-HTLV-III positive individuals.

Previously, HTLV-III antigen has been detected in vitro by lymphocyte isolation followed by tissue culture of these lymphocytes and their co-cultivation with a human T-cell line such as HT-9 susceptible to infection with HTLV-III. Presence of HTLV-III antigen is then detected in the cell culture by testing for reverse transcriptase activity or by immunofluorescent antibody or sandwich enzyme immunoassay techniques. The problem with this method is that it is extremely technique sensitive, labor intensive and requires special laboratory facilities and two to eight week incubation periods to obtain results.

McDougal, et al., *J. Immunol. Methods,* 76: 171–183 (1985) have described a method for detecting lymphadenopathy-associated virus (LAV) in supernates of LAV-infected human lymphocyte cultures. LAV, like HTLV-III, is considered a prototype strain of the human retrovirus thought to be the causative agent of AIDS.

In McDougal's method, LAV is propagated in lymphoblasts, and the culture supernates are monitored for viral infection by direct immunofluorescence, enzyme-linked immunosorbent (ELISA) capture assay and by supernate reverse transcriptase activity. In the LAV-ELISA capture assay, microtiter plate reaction wells are coated with human anti-LAV IgG, the culture supernates to be tested are added to the wells, incubated and washed, and horseradish peroxidase conjugated human anti-LAV IgG is added to the wells. After incubation and washing, an o-phenylenediamine (OPD)/$H_2O_2$ solution is added, color is developed and the optical density in the reaction walls is read in an automatic microtiter plate reader at 490 nm.

The problem with the McDougal et al. method is that it is applicable only to the assay of tissue culture supernates and, cannot be performed on human biological samples due to the likelihood of detecting false positives. The reason false positives occur in the McDougal, et al. procedure is that the human antibody used for the coating of reaction wells and in the conjugate, will react with other antigens in the human sample such as rheumatoid factor.

An easier method of detecting HTLV-III viral antigen directly from biological samples is desirable. However, it has been suggested that HTLV-III viral antigens are present in such low concentrations, if at all, in some biological samples that they would not be readily detectable. Therefore, some manipulation of whole blood samples such as lymphocyte separation followed by lysis, or small-scale lymphocyte cultivation, might be necessary in order to effectively detect viral antigen. Another potential problem in detection of HTLV-III viral antigen in biological samples is the simultaneous presence of anti-HTLV-III, leading to immune complex formation and possible masking of the HTLV-III antigens. Methods for dissociating HTLV-III antigen from immune complexes would allow for antigen detection, but would require additional processing of the sample.

SUMMARY OF INVENTION

The invention is a direct immunoassay procedure for detection of HTLV-III antigen in biological samples. The assay utilizes a labeled second antibody to achieve the necessary sensitivity required for detection of low levels of HTLV-III viral antigen. The assay comprises:

(1) coating a solid support with antibody to HTLV-III;

(2) contacting the coated solid support with a biological sample;

(3) contacting the solid support with antibody to HTLV-III from a different animal species than that utilized in step 1;

(4) contacting the solid support with an antibody specific for the antibody of step 3, and conjugated to a label such as an enzyme, radioisotope or fluorescent label; and (5) detecting the label as a measure of the presence of HTLV-III viral antigen in the sample.

Biological samples which are easily tested by the method of the present invention include human and animal body fluids and tissues, tissue culture media and recombinate DNA materials. Solid supports which can be used in the immunoassay of the invention include wells of reaction trays, test tubes, beads, strips or other solid supports which are well known to those skilled in the art.

Both polyclonal and monoclonal antibodies are useful as reagents in the present invention. Also, IgG and IgM antibodies may be used.

DETAILED DESCRIPTION OF THE INVENTION

The following examples are illustrative of the immunoassay of the present invention.

EXAMPLE I

This example demonstrates an immunoassay for HTLV-III antigen in a human biological sample.

1. A human anti-HTLV-III IgG-coated ¼ inch polystyrene bead is contacted with 200 µl sample such as serum, plasma, or other biological solutions, for 2 to 24 hours and preferably about 14 to 18 hours, at a temperature in the range of 20° C. to 45° C. and preferably at about room temperature. The bead is then washed three times with 5 ml distilled water to remove any unbound sample.

2. The washed bead is contacted with 200 µl of rabbit anti-HTLV-III IgG and incubated for 2 to 24 hours and preferably for about 2 hours at a temperature of about 20° C. to 45° C. and preferably at about 40° C. to 45° C. The bead is then washed as described in step 1 to remove any unbound reagent.

3. The washed bead is contacted with 200 µl of goat anti-rabbit IgG conjugated to horseradish peroxidase, and incubated for 1 to 4 hours and preferably 2 hours at a temperature in the range of 20° C. to 45° C. and preferably at 40° C. to 45° C. The bead is again washed as described in step 1.

4. The washed bead is contacted with 300 µl of o-phenylenediamine-hydrogen peroxide solution which forms a yellow colored product in the presence of horseradish peroxidase, and after incubating for approximately 30 minutes at room temperature, 1 ml of 1N H$_2$SO$_4$ is added.

5. Absorbance is read at 492 nm using a standard spectrophotometer.

Steps 2 and 3 of the assay method of Example I. may optionally be combined into one step to facilitate the assay procedure. Also, IgM antibodies may be substituted for the IgG antibodies of steps 1 and 3.

EXAMPLE II.

Sera from patients with AIDS, AIDS related complex (ARC), asymptomatic sexual contacts of patients with AIDS, and patients with other underlying diseases not at risk for AIDS, were tested with the assay described in Example I. and with a commercially available assay for antibody to HTLV-III (Abbott Laboratories, North Chicago, Ill.) (Table 1). Ninety-one percent of 70 serum samples from 26 patients with AIDS were antibody positive, and 67% were antigen positive. Antigen was detected in at least one serum sample from 18 to 26 AIDS patients, giving an antigen positivity rate of 69% in this population. Six (8.6%) of 70 sera from patients with AIDS were antigen positive/antibody negative, although all six were from one (3.8%) of the 26 AIDS patients. Overall, in the group consisting of AIDS, ARC and AIDS contacts, 5.3% were antigen positive/antibody negative, corresponding to two (2.3%) of 86 in these groups. Similarly, Salahuddin, et. al., *Lancet*, 1984-II: 1418-1420 (1984), were able to isolate HTLV-III virus from lymphocytes of four (4.2%) of 96 patients with AIDS, ARC, or asymptomatic individuals at high risk for contracting AIDS who were anti-HTLV-III negative.

EXAMPLE III.

The specificity of the assay was determined using 200 human plasma and serum samples, from selected blood donors, negative for Hepatitis markers and anti-HTLV-III, as well as the 47 control patient samples (Table 1). No antigen false positives were seen. All negative values were within two standard deviations of the negative control mean, and the cutoff was five standard deviations from the negative control mean.

TABLE 1

HTLV-III Antigen and Antibody Enzyme Immunoassay Results of Serum Samples

| Sample Group | No. Patients | No. Samples Tested | Antigen + | Antibody + | Antigen and Antibody + | Antigen +/ Antibody − |
|---|---|---|---|---|---|---|
| AIDS | 26 | 70 | 47 | 64 | 41 | 6 |
| ARC | 50 | 53 | 5 | 28 | 4 | 1 |
| AIDS Contacts | 10 | 10 | 1 | 5 | 1 | 0 |
| Controls | 47 | 47 | 0 | 0 | 0 | 0 |

The identification of biological samples which are positive for HTLV-III antigen but negative for anti-HTLV-III is important in the screening and protection of human blood supplies. This assay enables a quick screening procedure for detecting individuals infected with HTLV-III virus who are anti-HTLV-III negative, and therefore not indicated as HTLV-III positive by current available antibody screening tests. Also, the detection of HTLV-III viral antigen by the assay of the present invention may have diagnostic and prognostic value for AIDS patients and may also prove useful in monitoring patients undergoing anti-viral therapy.

While specific examples have been given to illustrate the invention, it is to be understood that those skilled in the art will recognize variations without departing from the spirit and scope of the invention.

What is claimed is:

1. An immunoassay for the detection of viral antigens in a biological sample comprising:
    (a) coating a solid support with antibody to HTLV-III from a first animal species;
    (b) contacting the coated solid support with the biological sample so as to form a conjugate;
    (c) contacting the conjugate with antibody to HTLV-III from a second animal species;
    (d) contacting the conjugate with a labeled antibody specific for the antibody of said second animal species; and
    (e) detecting the label as a measure of the presence of HTLV-III viral antigen in the sample.

2. The immunoassay of claim 1 wherein steps c and d are performed simultaneously.

3. The immunoassay of claim 1 wherein the antibodies of steps a and c are IgG or IgM antibodies.

4. The immunoassay of claim 1 wherein the label is horseradish peroxidase.

5. The immunoassay of claim 1 wherein said label is selected from the group consisting of enzymes, radioisotopes of fluorescent labels.

6. An immunoassay for the detection of HTLV-III viral antigens in a human biological sample comprising:
    a. coating a polystyrene bead with human anti-HTLV-III IgG;
    b. contacting the coated bead with the sample, incubating and washing;
    c. contacting the bead with rabbit anti-HTLV-III IgG, incubating and washing;
    d. contacting the bead with goat anti-rabbit IgG conjugated to horseradish peroxidase, incubating and washing;
    e. contacting the bead with an o-phenylenediamine-hydrogen peroxide solution; and
    f. measuring the absorbance of the color product formed at 492 nm to determine the presence of HTLV-III viral antigen in the sample.

* * * * *

UNITED STATES PATENT AND TRADEMARK OFFICE
CERTIFICATE OF CORRECTION

PATENT NO. : 4,748,110

DATED : May 31, 1988

INVENTOR(S) : Deborah A. Paul

It is certified that error appears in the above-identified patent and that said Letters Patent is hereby corrected as shown below:

In Column 2, Line 28, delete "recombinate", and substitute therefor, "recombinant".

In Column 3, Line 43, delete "selected", and substitute therefor, "unselected".

In Column 3, In Table 1, the last Column in the Headings, delete "Antigen +/Antigen body -", and substitute therefor, "Antigen +/Antibody -".

In Column 4, In Table 1-continued, the last Column in the Headings, delete "Antigen +/Antigen body -", and substitute therefor, "Antigen +/Antibody -".

In Column 4, Line 49, delete "of", and substitute therefor, "or".

Signed and Sealed this

Fifteenth Day of November, 1988

Attest:

DONALD J. QUIGG

*Attesting Officer*  *Commissioner of Patents and Trademarks*